United States Patent [19]

Hildebrand et al.

[11] 4,444,497
[45] * Apr. 24, 1984

[54] UNIFORM SAMPLE TRANSPORT AND MANIPULATION SYSTEM AND METHOD FOR SPECTROMETERS

[75] Inventors: Karl J. Hildebrand, Tyngsboro; John Leeman, Andover, both of Mass.

[73] Assignee: Leeman Labs, Inc., Lowell, Mass.

[*] Notice: The portion of the term of this patent subsequent to Aug. 2, 2000 has been disclaimed.

[21] Appl. No.: 320,668

[22] Filed: Nov. 12, 1981

Related U.S. Application Data

[63] Continuation-in-part of Ser. No. 260,334, May 4, 1981, Pat. No. 4,396,287.

[51] Int. Cl.$^3$ ............................................. G01N 21/74
[52] U.S. Cl. ..................................... 356/244; 356/316
[58] Field of Search .................. 356/36, 38, 311, 312, 356/313, 314, 315, 316, 317

[56] References Cited

U.S. PATENT DOCUMENTS

| | | | |
|---|---|---|---|
| 3,174,393 | 3/1965 | Dewey et al. | 356/315 |
| 3,586,446 | 6/1971 | Findl et al. | 356/36 |
| 3,832,060 | 8/1974 | Dahlquist | 356/312 |

Primary Examiner—F. L. Evans
Assistant Examiner—L. A. Dietert
Attorney, Agent, or Firm—John M. Brandt

[57] ABSTRACT

A sample transport and manipulation system and method for exciting a quantitatively uniform sample for spectrometric analysis over an extended period of time is disclosed. A uniform sample transport medium such as a filament is transported at a uniform rate through an excitation situs which is coincident with the optical input situs of the spectrometer. Means for uniformly depositing a liquid sample over the medium are included to complete the establishment of a system in which the spectrometer is presented with a quantitatively uniform excited sample on a continuous basis.

2 Claims, 1 Drawing Figure

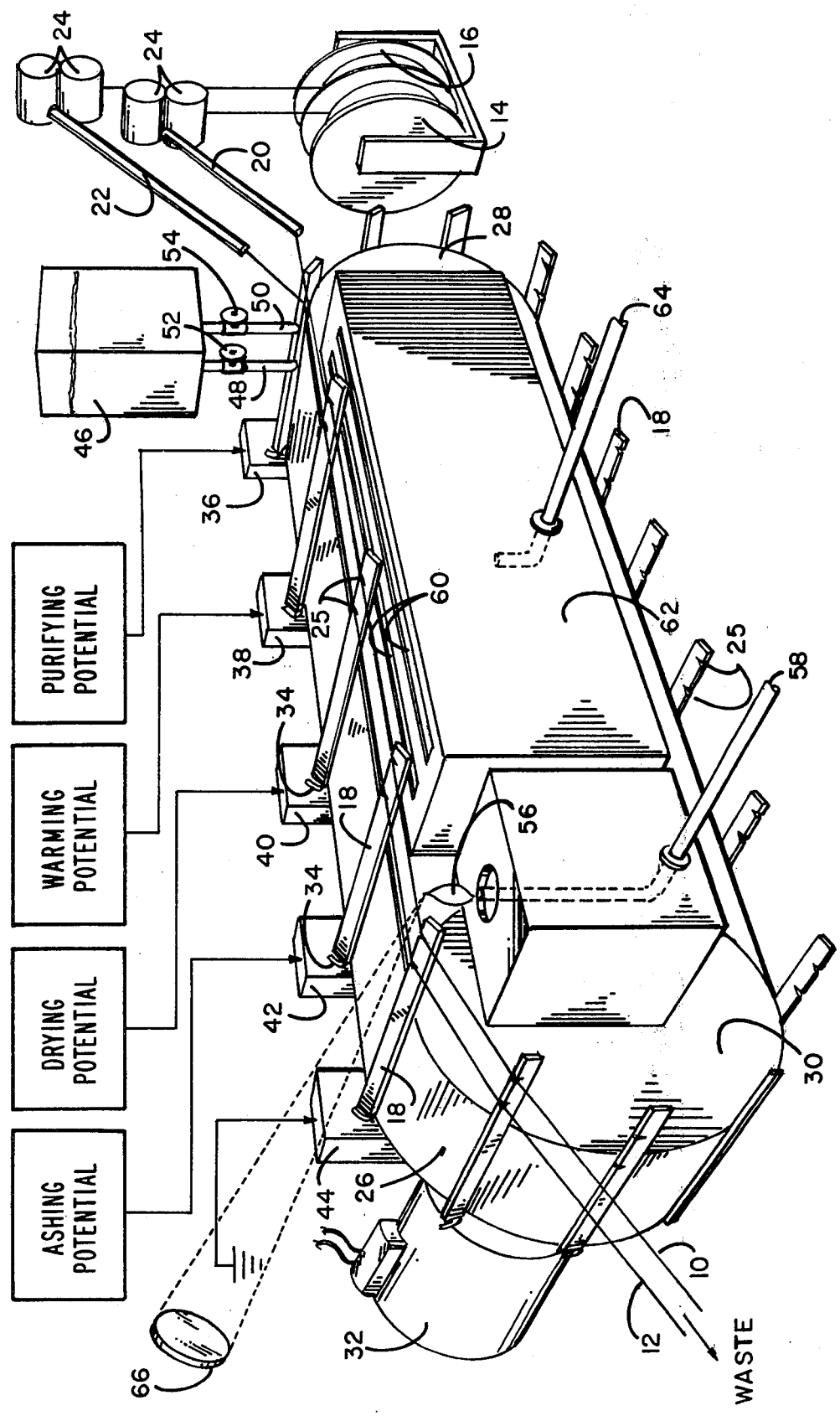

UNIFORM SAMPLE TRANSPORT AND MANIPULATION SYSTEM AND METHOD FOR SPECTROMETERS

CROSS REFERENCE TO RELATED APPLICATIONS

This application is a continuation in part of Ser. No. 06/260,334 filed May 4, 1981, now U.S. Pat. No. 4,396,287, entitled Sample Manipulation System for Spectrometers by the same inventors.

BACKGROUND OF THE INVENTION

1. Field of the Invention

The invention resides in the field of analytical spectrometers and more particularly relates to devices for transporting and manipulating a sample for presentation to the optical input of such spectrometers.

2. Description of the Prior Art

In the majority of prior art spectrometers, a quantity of sample is placed in a fixed position in an excitation device and heated until it is consumed. For reference, a variety of flame and non-flame excitation devices exist. Among the non-flame devices are arcs and plasma jets, illustrations of which are shown, for example, in U.S. Pat. Nos. 4,009,413, Elliot et al., and 4,147,957, Hildebrand. Inductively coupled plasma furnaces are also widely used.

In the above devices, the sample quantity and position and consequently the duration of excitation per sample remain fixed and limited. In multi-element analysis, it is often necessary to measure the intensity of a number of different wave lengths which appear in various spatial positions at the output focal plane. Time will therefore limit the number of such measurements which can be made for a single sample before the sample is consumed.

One solution to the problem of limited excitation time is to photograph the entire output spectrum of the short duration excitation for later analysis. Another is to reintroduce further specimens of the same sample and repeat the excitation and measurement process at different wave lengths. Another is to employ an array of detectors, spatially arranged to simultaneously measure a plurality of wavelengths.

The invention disclosed herein, in contrast to the above prior art devices, allows a continuous measurement and analysis to be carried out. This is accomplished by depositing a dissolved sample contained in a liquid or solvent uniformly over a uniform transport medium, preferably a length of filament, and then transporting the filament through the excitation situs of the spectrometer at a uniform rate. The filament is preferably, although not necessarily, electrically conductive and of a configuration to which the sample solution will adhere well and in some quantity.

It is a substantial advantage to be able to carry out continuous analysis as consecutive uniform portions of a sample are presented to the spectrometer. For example, a plurality of programmed scans by the spectrometer photodetection system may be conducted to determine the presence or absence of a number of elements. Additionally, background noise corrections may be made intermittently between scans. A high rate of sampling of the products of industrial processes including pollutants may be carried out and a complete, quantitative and qualitative analysis of each sample concluded on an automatic or semi-automatic basis. Errors which may occur when reintroducing samples in prior art fixed systems are eliminated.

SUMMARY OF THE INVENTION

The invention may be summarized as a sample transport and manipulation system and method for exciting a quantitatively uniform sample for spectrometric analysis over an extended period of time.

The apparatus comprises means for uniformly depositing a dissolved sample over a portion of a uniform transport medium such as a graphite fiber and means for transporting at a uniform rate the sample bearing medium through an excitation device having a excitation situs coincident with the optical input situs of the spectrometer.

The method of the invention may be described as essentially the process of utilizing the above mentioned apparatus, i.e. uniform sample disposition upon and transport at a uniform rate of a transport medium of uniform configuration. Although a graphite fiber is the preferred transport medium, it is intended that any device which will support or contain the sample in a uniform quantity over a transportable length be included within the definition of uniform transport medium. Thus a sample holding groove within a rotating disc would serve as well as a fiber or filament.

The features and advantages of the invention will become more evident from the description of the preferred embodiment and drawing which follow.

DESCRIPTION OF THE DRAWING

The drawing is a perspective, partially schematic view of the preferred embodiment of the invention.

DESCRIPTION OF THE PREFERRED EMBODIMENT

Referring to the FIGURE, the preferred embodiment of the invention is illustrated in which electrically conducting graphite filaments or braid of uniform diameter 10 and 12, wound on spools 14 and 16, are supplied to transport clamps 18 through leads 20 and 22. Tensioning rollers 24 restrained by spring loading means not shown provide sufficient resistance to render the filaments taut. The clamps consist of electrically conducting bars into which are cut V grooves 25 which function to bind the filaments at their apex. The clamps are attached to and transported by insulating belt 26 stretched between rotatable roller 28 and rotatable roller 30, driven by a constant speed, synchronous electrical motor 32. The bars are inclined at a slight angle to facilitate the binding action.

Each clamp bar has an electrical contact 34 positioned at the end opposite the V grooves to engage electrical power supply contact bars 36, 38, 40, 42, and 44. The clamp bar contact may be a wiper spring as shown or a roller, or any other convenient device.

Each contact bar is supplied with a separate level of electrical power or potential. For example, bar 36 is supplied with sufficient power for purifying the braid, bar 38 to create dispensation affinity, bar 40 for desolvation, and bar 42 for ashing. Bar 44 serves as a ground.

Liquid sample is uniformly dispensed from reservoir 46 through pipes 48 and 50 on to the braid. Dispensation rate is controlled by stopcocks 52 and 54. Other uniform dispensing means such as syringes and peristaltic pumps, well known in the art for their accuracy, may also be used. A plasma excitation device employed to excite the sample on the braid to energy levels sufficient for spectrometric analysis is shown at 56. A jet of argon surrounds the plasma and is delivered to the excitation region through pipe 58.

To prevent contamination, the braid is constantly subjected to an argon bath supplied through exit ports 60 in distribution chamber 62 and supplied from pipe 64. Imaging of the excitation region is accomplished by any well known optical system represented in part by focusing lens 66.

An instrument substantially identical to that described above has been successfully operated using one-eight inch diameter graphite braid travelling at a feed rate of from four to twelve inches per minute. Sample dispensation is metered at one-tenth milliliter at a rate commensurate with the feed rate. Excitation time is typically sixteen to eighteen seconds. Reproducable results are obtained when the uniformity of the operating perimeters is held to approximately ±5%.

What is claimed is:

1. In a spectrometer having an optical input situs coincident with the excitation situs of a sample excitation device, a sample transport and manipulation system for exciting a quantitatively uniform sample for analysis over an extended period of time comprising in combination:
   a. a quantity of electrically conductive uniform sample transport medium;
   b. means for supporting said medium;
   c. means for uniformly depositing a sample in solution over a portion of said medium;
   d. means for heating said medium comprising a variable electrical power source comprising:
      1. a plurality of separate contact points;
      2. means for applying variable levels of electrical power to each of said separate points; and
      3. means for sequentially connecting separate portions of said medium to said separate points; and
   e. means for transporting said portion and said sample at a uniform rate through said excitation situs for excitation whereby successive quantitatively uniform portions of said excited sample are sequentially exposed to said spectrometer at a uniform rate for analysis.

2. The apparatus of claim 1 wherein said medium comprises graphite braid.

* * * * *